(12) United States Patent
Bacon et al.

(10) Patent No.: US 12,343,282 B2
(45) Date of Patent: Jul. 1, 2025

(54) FLUID DELIVERY DEVICES

(71) Applicant: DISPENSER TECHNOLOGIES LIMITED, Waterlooville (GB)

(72) Inventors: Raymond John Bacon, Waterlooville (GB); Benjamin Peter Hall, Waterlooville (GB)

(73) Assignee: DISPENSER TECHNOLOGIES LIMITED, Waterlooville (GB)

( * ) Notice: Subject to any disclaimer, the term of this patent is extended or adjusted under 35 U.S.C. 154(b) by 281 days.

(21) Appl. No.: 18/009,539

(22) PCT Filed: Jun. 11, 2021

(86) PCT No.: PCT/GB2021/051462
§ 371 (c)(1),
(2) Date: Dec. 9, 2022

(87) PCT Pub. No.: WO2021/250426
PCT Pub. Date: Dec. 16, 2021

(65) Prior Publication Data
US 2023/0233370 A1 Jul. 27, 2023

(30) Foreign Application Priority Data
Jun. 11, 2020 (GB) .................................... 2008867

(51) Int. Cl.
*A61F 9/00* (2006.01)
*A61J 1/14* (2023.01)
(52) U.S. Cl.
CPC ............... *A61F 9/0008* (2013.01); *A61J 1/14* (2013.01)

(58) Field of Classification Search
CPC ..... A61F 9/0008; A61F 9/0026; A61M 15/08; A61M 15/009; B05B 11/0038;
(Continued)

(56) References Cited

U.S. PATENT DOCUMENTS 2,715,980 A * 8/1955 Frick ...................... B65D 49/08
137/853
3,963,147 A 6/1976 Waters
(Continued)

FOREIGN PATENT DOCUMENTS

EP 0 352 915 1/1990
EP 2 611 483 7/2013
(Continued)

OTHER PUBLICATIONS

International Search Report issued Oct. 14, 2021, in International (PCT) Application No. PCT/GB2021/051462, 5 pages.
(Continued)

*Primary Examiner* — Guy K Townsend
*Assistant Examiner* — Seth Han
(74) *Attorney, Agent, or Firm* — Wenderoth, Lind & Ponack, L.L.P.

(57) ABSTRACT

A device for dispensing a metered dose of fluid is provided. The device comprises a housing comprising: a non-pressurised reservoir sized to accommodate a plurality of doses of fluid; a springloaded metering chamber sized to hold at least a single dose of fluid; a first valve enabling fluid communication between the reservoir and the metering chamber; and a kink valve enabling the fluid in the metering chamber to exit the device.

18 Claims, 15 Drawing Sheets

(58) Field of Classification Search
CPC . B05B 11/1032; B05B 11/026; B05B 11/007; B05B 11/1067; B65D 35/28; B65D 83/0055

See application file for complete search history.

(56) References Cited

U.S. PATENT DOCUMENTS

| | | |
|---|---|---|
| 10,022,266 B2 | 7/2018 | Claret et al. |
| 2007/0095853 A1 | 5/2007 | Bonney et al. |
| 2010/0174248 A1* | 7/2010 | Wu .................. A61F 9/0008 222/562 |
| 2013/0168415 A1* | 7/2013 | Bacon ................ A61M 16/20 222/394 |
| 2013/0312739 A1* | 11/2013 | Rome .............. A61M 15/0065 128/200.22 |
| 2014/0008366 A1* | 1/2014 | Genosar .............. A61J 1/2096 220/265 |
| 2015/0351960 A1* | 12/2015 | Cooper ................ A61F 9/0026 604/521 |
| 2018/0312290 A1* | 11/2018 | Uchihashi ................ B65D 1/02 |
| 2020/0122172 A1* | 4/2020 | Tortosa Maroto ..... B65D 77/06 |

FOREIGN PATENT DOCUMENTS

| | | |
|---|---|---|
| WO | 98/41254 | 9/1998 |
| WO | 02/45783 | 6/2002 |
| WO | 2007/029019 | 3/2007 |
| WO | 2011/126569 | 10/2011 |
| WO | 2019/038269 | 2/2019 |

OTHER PUBLICATIONS

Written Opinion of the International Searching Authority issued Oct. 14, 2021, in International (PCT) Application No. PCT/GB2021/051462, 5 pages.

Patents Act 1977: Search Report under Section 17 issued Dec. 7, 2020, in corresponding GB Application No. 2008867.0, 1 page.

* cited by examiner

FLUID DELIVERY DEVICES

The present invention relates to improvements in fluid delivery devices and, more particularly, to devices for measuring and dispensing multiple doses of fluid from a reservoir. The fluid may be a medicament, in particular a liquid medicament for application to the eyes of a user, e.g. an eye drop.

Administering eye drops can be challenging in terms of both reliability of dosage size and reliability of targeting the dose. Eye drops are typically administered from a bottle provided with a nozzle or tapered tip and the bottle must be squeezed by the user. Typically, a drop forms on the tip of the bottle, where it grows, held in place by the surface tension of the fluid. The size of the dose is therefore at least partially defined by the viscosity of the fluid and therefore the size of droplet that can bead onto the nozzle before it drips or falls off. The timing of the release of the droplet is therefore unpredictable and the user's blink reflex may be sufficient to prevent effective transfer of the fluid into the eye of the user. Typically, the administration of the dose from a bottle arises from squeezing the bottle and the force required to achieve release of a droplet is relatively high which can result in hand shake in the user which affects aim and can result in the dose failing to reach the eye effectively.

Furthermore, relying on the droplet to fall from the nozzle tip, under gravity, leads to a requirement for the user to contort themselves such that the dose of medicament can be dispensed in a vertically downwards direction. This is challenging or even impossible for a sub-set of the intended users of these devices.

It is against this background that the present invention has arisen.

According to the present invention, there is provided a device for dispensing a metered dose of fluid, the device comprising a housing encapsulating: a reservoir sized to accommodate a plurality of doses of fluid; a spring-loaded metering chamber sized to hold at least a single dose of fluid; a first valve enabling fluid communication between the reservoir and the metering chamber; and second valve, which may be a kink valve, enabling the fluid in the metering chamber to exit the device.

The provision of a reservoir and associated metering chamber enables the dispensing of multiple doses, rather than being a single use device.

A kink valve is a valve formed by folding a pliable conduit so that the material from which the conduit is formed folds in on itself and substantially halts the flow of fluid through the conduit. The angle through which a first part of the conduit is rotated relative to a second part of the conduit to initiate fluid flow may be referred to as the actuation angle. Actuation of the valve involves the valve moving from a closed or sealed position, into an open position such that fluid may flow therethrough. There may be some hysteresis in the opening and closing cycle. Kink valves are advantageous because they do not require multiple separate parts to be manufactured in tight tolerances. Furthermore their mode of operation is such that precise setting of the angle at which the kink is formed is not required. The angle must merely exceed the threshold value to open or close the valve.

A kink valve generally has a low actuation force so the valve can be opened without the requirement for excessive force that can result in hand shake and, therefore, misalignment between the ejected dose and the user's eye.

The reservoir, metering chamber and two valves can be formed as a single pouch that is formed from the same material throughout, either as a single piece or two substantially flexible planar sheets. Once the single piece is folded suitably or two substantially planar sheets of the material are brought together, the piece or pieces are welded, adhered or bonded together to form the reservoir, metering chamber and first and second conduits including the respective first and second valves.

However, in some embodiments, the reservoir, metering chamber and two valves may be formed as a single pouch from a plurality of different sheets and/or a plurality of different materials. For example, 2, 3, 4, 5 or more than 5 different sheets may be used. Each sheet may be a different material.

The pouch is capable of deforming to change its internal volume and therefore receive fluid to be dispensed. When the pouch contains fluid, up to the maximum volume of the pouch, the pouch is non-pressurised. That is, the shape of the pouch has changed by deflecting, not stretching, the walls away from one another to create a volume in which the fluid is held. Alternatively, or in addition, the pouch may be substantially non-pressurised. That is, the pressure within the pouch is not enough to cause the fluid to flow from the reservoir into the metering chamber. As a result, the reservoir is pressurised only during metering, when fluid is moved from the reservoir into the metering chamber.

Alternatively, the reservoir and the metering chamber may be two distinct pouches that are joined to form a single pouch. Consequently, the reservoir may be formed as a single pouch that is formed from the same material throughout, either as a single piece or two substantially flexible planar sheets. Moreover, the metering chamber may be formed as a single pouch that is formed from the same material throughout, either as a single piece or two substantially flexible planar sheets. The two pouches may be welded, adhered or bonded together in the vicinity of the first valve.

Moreover, excess material of the reservoir pouch may be configured to generate the first valve. For example, excess material of the reservoir pouch may be inserted into the metering chamber pouch and configured to generate a flat valve. The join between the external surface of the reservoir pouch and the internal surface of the metering pouch may be welded, adhered or bonded together, thus preventing the flow of fluid therebetween.

Alternatively, the reservoir can be provided as a bellows bottle or syringe. This fulfils the same requirements as the reservoir in the pouch based example described above in that the reservoir is able to change volume without being pressurised. In other words, a non-pressurised filled state is possible.

Each substantially planar sheet may be formed from the same flexible, not stretchy material. A non-stretchy material may also be non-elastic. The flexibility of the material is critical for the creation of the valves. For the valves to function effectively, it is also important that the material is substantially non-elastic.

The metering chamber is biased to a low volume configuration by the presence of a metering chamber spring. The metering chamber spring may be a leaf spring. The biasing force of the metering chamber spring provides the force required to eject or dispense the metered dose from the device. The metering chamber spring changes the volume of the metering chamber from a first volume to a second, smaller volume wherein the difference between these volumes is a metered dose. The second volume may be zero, or close to zero.

The first valve may be a one-way valve. Alternatively, or in addition, the first valve may be a non-return valve. For example, the first valve may be a flat valve. The flat valve may also be known as a duck bill valve or a prayer valve. The flat valve may comprise two pieces of material laid flat against each other. The two pieces of material may be a part of the pouch. More specifically, the two pieces of material may be a part of the reservoir. However, in some embodiments, the two pieces of material are discrete piece of material that are subsequently joined to the pouch. The valve may protrude into the metering chamber. More specifically, the two pieces of material may protrude into the metering chamber. The two pieces of material may be configured to form a one-way valve. Consequently, as the pressure in the metering chamber increases during metering, the pressure on the outside of the valve seals the two pieces of material against each other and prevents the fluid from flowing back into the reservoir. The two pieces of material may be a part of the pouch. In some embodiments, the two pieces of material may be a part of the distinct reservoir pouch.

Alternatively, the flat valve may comprise a single piece of material configured to lie against a wall of the metering chamber. More specifically, the wall of the metering chamber may be a side wall or a front wall or back wall. Consequently, one of the walls of the metering chamber may be the second piece of material required to generate the flat valve. Accordingly, as the pressure in the metering chamber increases during metering, the pressure on the outside of the valve seals the piece of material against the metering chamber side wall, thus preventing the fluid from flowing back into the reservoir. The single piece of material may be a part of the pouch. In some embodiments, the single piece of material may be a part of the distinct reservoir pouch.

Alternatively, the first valve may be a winkle valve. A winkle valve is formed where there is a change in width between the reservoir and the conduit. The change in width can be gradual, such as a taper or it can be a step change. As the pouch reservoir is filled, this change in width causes a specific form of deformation of the polymer sheets from which the pouch is fabricated. A crease forms within the conduit that is arrow shaped in the direction in which fluid would otherwise flow. This arrow shaped crease blocks the flow of fluid through the conduit and thereby keeps the conduit closed preventing fluid from flowing in either direction through the conduit in which the crease is formed until a threshold pressure is exceeded overcoming the deformations to enable some fluid to flow through the conduit. In some cases, a winkle valve may also incorporate a kink valve as described above.

The first valve may be formed in a first conduit linking the reservoir and the metering chamber and the kink valve may be formed in a second conduit linking the reservoir and an outlet. More specifically, the kink valve may be formed in a second conduit linking the metering chamber and an outlet. Each conduit may be formed between the two substantially planar sheets, which lie flat when the device is not in use. Each conduit can therefore be defined as having a width that extends in the direction perpendicular to the direction of fluid flow. The first conduit extends from the reservoir to the metering chamber and the second conduit extends from the metering chamber to a nozzle or outlet.

The outlet may be provided with a nozzle. The nozzle is provided towards the end of the second conduit and it manages the departure of the fluid from the device. The fluid is ejected from the device and the nozzle controls the direction and force with which the fluid is ejected. The nozzle may be tapered and therefore increase the velocity of the fluid as it exits the device ensuring that the fluid overcomes its own surface tension that might otherwise result in the fluid beading on the surface of the device. Instead, the nozzle ensures that the surface tension is overcome and the fluid is ejected in the desired direction. The desired direction may be horizontal. Alternatively, it may be an upward or downward trajectory from the nozzle.

The housing may comprise an outlet port configured to enable the metered dose to be ejected from the housing. Accordingly, the outlet port may be an aperture configured to line up with the nozzle. The cross-section of the outlet port may be larger than the cross-section of the nozzle. For example, the outlet port may be elongate. A housing comprising an elongate outlet port reduces the risk of the metered dose from building up the outlet port.

Furthermore, the nozzle can be used to define characteristics of the droplet stream in which the fluid leaves the device. Depending on the selection of the nozzle, the fluid can be provided in a single, relatively large droplet. Conversely, the fluid can be provided as a stream of tiny droplets; a fine spray; a baffled stream. The speed at which the fluid leaves the device is also controlled by the nozzle.

A dose may typically be 40 µl to 50 µl, although this may be provided in a number of droplets. However, in some variants the dose could be less or substantially more e.g. 5 ml.

The first and/or second conduit may have a constant width. It also means that the position of the valves along each of the conduits is not critical as the conduit has a constant width. Conversely, in some embodiments, one of the conduits, in particular the second conduit, may be tapered in the flow direction. This increases the velocity of the fluid as it exits the device through the nozzle. This, in turn, ensures that the fluid is ejected from the device as the force and flow of the fluid exceeds the surface tension.

The first conduit may have a width of between 2 mm and 9 mm. Maximising the width of the first conduit maximises the rate at which the metering chamber can be filled from the reservoir. Maximising the width of the first conduit also reduces the pressure required to transfer the fluid from the reservoir into the metering chamber.

The second conduit may have a width of between 2 mm and 9 mm. This range of valve widths enables efficient expulsion of the metered dose from the pouch. This range of widths of the valve enables this substantially horizontal emission of the metered dose to be achieved.

The kink valve may typically have an actuation angle of between 20° and 70°. This range of angles enables the kink valve and, thereby, the ejection of the fluid to be controlled in a compact manner. Minimising the stroke to around 20° is advantageous in this regard.

The housing may include a trigger configured to actuate the kink valve and thereby dispense the metered dose of fluid from the device. The trigger may be a button, which moves through the housing. For example, the trigger may be a dispenser or a dispenser button. Moreover, the dispenser button may be configured to transfer compression by a user into a rotation of the second conduit.

The dispenser button may comprise a dispenser button spring. The dispenser button spring may be an over centre spring. The force ramp down on the spring may be so quick that once the button has started to deploy, it will automatically deploy completely. Consequently, it is very unlikely that the dispenser button will halt part-way through its actuation. This ensures that the second valve opens rapidly, thus providing a more consistent trajectory.

In some embodiments comprising a kink valve, the housing may include an edge over which the kink valve is folded. The edge may be provided on the trigger. The pouch may be adhered to the trigger at or around the edge. The provision of an edge over which the kink valve is folded helps to define the exact location of the kink valve and also contributes to a reduction in the angle required to achieve the kink. The difference in angle between the open and close positions is reduced in embodiments which include an edge over which the kink valve is folded. The conduit is preferably folded towards the edge to achieve closure of the kink valve.

The kink valve may have an actuation force of less than 3 N. Furthermore, the actuation force of the kink valve may be set between 1 N and 3 N. In some embodiments the actuation force may be less than 1 N, less than 0.5 N, for example 0.15 N.

It is important for the accuracy and ease of use of the device that the actuation force of the kink valve, which results in the metered dose being ejected from the pouch, is low. If a considerable force is required it is likely to result in the movement of the device relative to the intended target. Furthermore, it may preclude use by certain intended user groups such as those of advanced years or some level of disability.

In some embodiments, the reservoir may further comprise a burstable seal. The burstable seal retains the fluid towards the end of the reservoir furthest from the conduit and valve prior to the first use of the pouch. Depending on the shelf life of the contents of the pouch, the pouch may be stored for some time and, in the absence of the burstable seal there would be some pressure on the first valve throughout the time that the pouch is stored prior to first deployment. The burstable seal therefore protects the first valve from the pressure of the contents of the reservoir until the first metered dose is delivered and helps to protect the pouch contents from any potential contamination during storage.

The pouch may be formed from a plurality of layers of different polymers. For example, the pouch may be formed from metalised PET, or boppmet, which is a layered flexible polymer with a metalised film. When selecting the material, it is important that the reservoir and metering chamber are flexible, but do not stretch. This is important for the effective formation of the valves. Furthermore, the selected material must have a low gas permeability and low moisture vapour permeability. Most polymers allow oxygen/water vapour through and therefore the material may combine a plurality of layers, at least one of which must block transfer of moisture vapour and other gases.

The reservoir may comprise two chambers. For example, the reservoir may comprise a storage chamber and a prime chamber. The first valve may be formed in the first conduit, which may link the prime chamber and the metering chamber. The second valve may be formed in the second conduit, which may links the metering chamber and the outlet. Consequently, the prime chamber may be positioned between the storage chamber and the metering chamber.

The prime chamber may be configured to contain a smaller volume of fluid than the storage chamber. For example, the maximum volume of the prime chamber may be up to 50% of the maximum volume of the storage chamber. However, in some embodiments, the maximum volume of the prime chamber is up to 30%, 25%, 20% or 15% of the maximum volume of the storage chamber. Alternatively, or in addition, the prime chamber may be configured to contain a larger volume of fluid than the metering chamber. For example, the maximum volume of the prime chamber may be up to 500% of the maximum volume of the metering chamber. However, in some embodiments, the maximum volume of the prime chamber is up to 400%, 300%, 200%, 150% or 100% of the maximum volume of the metering chamber. This configuration of chambers improves the reliability with which a sufficient volume of fluid may be urged into the metering chamber.

The storage chamber may be in fluid communication with the prime chamber via a third conduit. The third conduit may comprise a third valve. The third valve may be a pinch valve. The pinch valve may comprise two surfaces configured to meet with enough pressure to form a seal, thus preventing the flow of fluid between the storage chamber and the prime chamber.

Alternatively, or in addition, the third valve may be a kink valve. Consequently, in some embodiments, the third valve may comprise both a kink valve and a pinch valve. Accordingly, the third valve may be a kinked pinch valve. The kinked pinch valve may comprise two tessellating surfaces configured to manipulate the third conduit into a kinked shape between the two surfaces when the valve is closed or sealed. The two surfaces may be angular. More specifically, each surface may comprise an angle that is greater than the actuation angle of the third conduit. This may increase the sealing force of the third valve compared to a kink valve or pinch valve alone.

The reservoir comprises a storage chamber and a prime chamber. The reservoir may comprise a bias configured to urge the fluid towards the prime chamber.

The bias ensures that when the third valve is opened the fluid moves from the storage chamber into the prime chamber. The bias ensures that the prime chamber is filled and fluid does not flow out of the prime chamber. The bias may be a spring configured to act on the pouch forming or containing the reservoir. The bias may be provided externally or internally to the reservoir. For example, the bias may be provided by forming the pouch from an elastic material which is stretched by the introduction of fluid. The bias may be provided, at least in part, by gravity if the device is held such that the prime chamber is below the storage chamber.

The reservoir, metering chamber and three valves may be formed as a single pouch that is formed from the same material throughout, either as a single piece or plurality of planar sheets. Each substantially planar sheet may be formed from the same material which may be flexible, but preferably not stretchy. However, in some embodiments, the reservoir, metering chamber and three valves may be formed as a single pouch from a plurality of sheets, wherein the plurality of sheets comprise a plurality of different materials. Consequently, each substantially planar sheet may be formed from a different material. For example, the storage chamber may be flexible and elastic whereas the prime chamber and the metering chamber may be flexible and non-elastic.

Consequently, the flexible and elastic material of the storage chamber may be used to bias the fluid therein towards the prime chamber.

The housing may include a substantially planar wall to which at least part of the pouch is affixed. The pouch may be adhered to the planar wall of the housing. Alternatively, or additionally, it may be mechanically fastened to the wall, for example, using a clip.

Alternatively, or additionally, the pouch may be affixed to the housing via at least one dowel. Accordingly, the edge of the pouch may comprise at least one hole configured to receive the at least one dowel. The at least one hole may be located in the portion of the pouch adjacent to the reservoir, metering chamber and/or conduits. More specifically, the at least one hole may be located in the portion of the pouch configured to bond the two substantially planar sheets. This prevents the fluid retaining portion of the pouch from being punctured. The at least one dowel may be affixed to the housing. Preferably, the housing comprises two dowels and the pouch comprises two holes. This allows the pouch to move as it empties and the shape changes.

The first valve may be a winkle valve. In particular, a part of the winkle valve may be adhered to the planar wall of the housing. This prevents unwanted movement of the part of the reservoir nearest to the winkle valve which, in turn prevents unwanted distortion of the valve that might interfere with its intended function.

The housing may further include a primer configured to cause fluid to pass through the first valve in order to enable fluid flow from the reservoir into the metering chamber.

Prior to first use, the metering chamber is normally empty and the first action that the user must take is to meter a dose. This metering action is achieved by activation of the primer to move fluid into the metering chamber.

In subsequent uses, there may be some fluid in the metering chamber and therefore the amount of fluid moved from the reservoir to the metering chamber may be less. It may merely top up the fluid that is already in the metering chamber so that the metering chamber contains at least a metered dose.

It is only when the primer enables the fluid to move into the metering chamber that the system is substantially pressurised. When the device is not in use, the system is substantially non-pressurised. This is very different from many state of the art systems which use a pressurised reservoir.

The primer may include a primer button which is pushed downwards, or inwards towards the centre of the housing in order to urge fluid from the reservoir into the metering chamber. Alternatively, the primer may include a sliding part which applies pressure to the reservoir as the sliding part moves in a first direction. However, it is important that the slider does not apply pressure to the reservoir on the return stroke. There are various different embodiments that can achieve this functionality.

The sliding part may be a user actuated part provided on the exterior of the housing. The sliding part may have an indentation that is sized to accommodate the user's thumb. This helps to make the actuation of the primer intuitive to the user.

In some embodiments, the primer is also configured to actuate the third valve. More specifically, the primer may be configured to close the third valve and prevent fluid flow between the storage chamber and the prime chamber. The primer may be configured to close the third valve prior to urging fluid to flow into the metering chamber.

For example, the primer may be pushed downwards, or inwards, to actuate the third valve, thus sealing the prime chamber. Subsequently, the primer may be configured to rotate in order to urge fluid from the reservoir into the metering chamber. More specifically, the primer may comprise a protrusion configured to actuate the third valve. Once the third valve has been actuated, the primer may be configured to rotate about the protrusion, thus urging fluid from the prime chamber into the metering chamber.

Alternatively, or in addition, the primer may comprise a sliding part configured to apply pressure to the prime chamber as the sliding part moves in the first direction. This pressure may urge the fluid from the prime chamber into the metering chamber. The sliding part may be coupled to at least one hook-shaped portion that applies pressure to the reservoir or, more specifically, the prime chamber. The hook-shaped portion may be affixed directly to the lower surface of the sliding part through an aperture in the housing. Direct connection between the hook-shaped portion and the slider part onto which the user places their thumb to actuate the primer provides positive feedback to the user confirming that the priming of the device has been effective. Furthermore, direct connection between these parts minimises the number of moving parts required and therefore the range of potential failure modes for the device. Keeping the device simple, minimising the number of parts that move relative to one another can simplify manufacture and reduce cost.

The primer may further comprise a spreader hingeably attached to the housing adjacent to the reservoir. The spreader ensures that the hook does not puncture the reservoir by spreading the applied pressure evenly across the width of the reservoir or, in some embodiments, the width of the prime chamber.

The primer may further comprise one or more wedges to bias the operation of the primer to apply pressure to the reservoir only when the sliding part moves in the first direction. The wedges are affixed to the spreader and/or to the lower surface of the sliding part of the primer. In some embodiments there are two wedges, one of which is attached to the spreader and one of which takes the place of the hook-shaped portion and is attached to the lower surface of the sliding part of the primer.

The housing may further comprise an indicator configured to confirm the presence of a metered dose within the metering chamber. It is important for the user to be aware of the status of the metering chamber. If it is empty, then the deployment of the dispenser button will not result in the egress of any fluid.

The indicator may be a translucent light guide. This enables light to undergo TIR to reach the end of the light guide which is visible to the user through an opening in the housing.

Alternatively, the indicator may be a brightly coloured peg. The brightly coloured peg may be configured to move into a more visible or prominent position when the metering chamber has been filled and therefore the device is ready for actuation.

For example, the peg may be located within a chamfered section of the housing. When the metering chamber is empty, the top of the peg may be level with the bottom of the chamfer. Accordingly, the side(s) of the peg will be located within the housing and will not be visible. Once the metering chamber has been filled, the peg may protrude from within the housing, thus exposing at least one side of the peg within the chamfer. In its protruded position, the top of the peg may be level with the external surface of the housing.

The surface of the chamfer may be a first colour. The top of the peg may be a second colour. At least one side of the peg may be a third colour. The first and second colour may be substantially the same. The third colour may be brighter than the first and second colour. Consequently, the brightly coloured side(s) of the peg may reflect off the chamfered surface, thus generating a coloured shape that is visible to the user, in use.

Alternatively, or additionally, the surface of the chamfer may be reflective. For example, the surface of the chamfer may comprise a foil sticker. Alternatively, the surface of the chamfer may comprise a shiny or glossy finish.

The housing may be provided with a cowl to protect the nozzle. The end of the nozzle from which the fluid is dispensed should not come into contact with anything that could interfere with its functionality or contaminate the fluid. This is especially critical as the device is not a single use device and therefore any contamination of the nozzle picked up during a first deployment or subsequent to a first deployment could impact on subsequent metered doses coming from the device.

Alternatively, or additionally, the trigger may be configured to protect the nozzle. More specifically, the trigger may comprise a plate configured to block and/or close the outlet port in the housing. When the trigger is pressed, the plate slides in a first direction, thus unblocking the outlet port and uncovering the nozzle. When the trigger is released, the plate may slide in a second direction, opposite to the first, and outlet port may be closed again, thus protecting the nozzle. The housing may further comprise an aiming aid. The aiming aid may be in the form of a bright circle provided around the outlet port. When the device is brought close to the eye when the fluid is an eye drop, then the bright circle will be too close to the user's eye for the user to clearly focus on the circle. However, the circle remains a positive indicator to the user as to the correct positioning of the device for the eye drops to be dispensed into the eye.

The device may further comprise a cap. The housing may be provided with a reduced thickness section around the outlet port end to accommodate the cap. The cap may comprise a first aperture configured to slide over the end of the device and cover the outlet port. Consequently the cap may be configured to engage with the device in a first orientation. The cap may have a width that substantially matches the housing such that, when the cap is on the device, the device has a constant thickness, thus avoiding any stepped edges that could catch and cause the cap to be accidentally removed.

The housing may be provided with a surface that is designed to pull the user's lower eye lid down and hold it down. The surface of the housing that is designed to pull the user's lower lid down may have a surface coating to engage with the user's skin and not slip. This tactile surface may include surface structures such as bumps or indentations so that the user does not have pull down the lower lid with one hand whilst holding the device in their other hand. This enables single handed operation of the device. Alternatively, in some variants, the cap may be configured to be reattached to the main housing after opening the device, to provide a surface to pull the user's lower eye lid down and hold it down.

In some embodiments, the cap further comprises a second aperture, perpendicular to the first, configured to pass over the end of the device and leave it exposed. Consequently, the cap may be configured to engage with the device in a second orientation. More specifically, the cap may be configured to pass over the end of the device and slide down over the primer button to prevent the trigger and the primer button from being pressed at the same time. Accordingly, the second aperture may be a hole that extends through the entire width of the cap. Moreover, in the second orientation, the cap may be used as an aid to lower the eye lid prior to actuation of the trigger.

The fluid may be a medicament or drug formulation. In particular, it may be eye drops.

As previously disclosed, the device may be reusable. The nozzle may be mounted on a nozzle plate. The nozzle plate may be configured to attach the nozzle to the pouch. The pouch and nozzle plate may be clipped into the housing. The housing may retain all the other components. The housing may comprise a slot configured to receive the nozzle plate. The slot may form a hinge configured to pivot the nozzle plate, in use. In some embodiments, the trigger may comprise a cam. Consequently, the line of actuation of the trigger may move closer to the nozzle's pivot as the trigger is pressed. This increases the angular rotation of the nozzle for a given trigger displacement and/or increasing the speed at which the nozzle rotates about the slot.

The trigger may be detachable. Alternatively, or additionally, the pouch, nozzle plate and trigger may be a single sub-assembly which is received by the housing. The housing may retain the metering chamber spring, primer button and bias. The reservoir, metering chamber and second valve may be integrally formed within the pouch. In some embodiments, the first valve is also integrally formed within the pouch.

In some embodiments, the pouch, nozzle plate, trigger, metering chamber and metering chamber spring may be a single sub assembly which is received by the housing. Consequently, the housing may comprise bias and the primer button. Alternatively, the first valve may be detachable from the first conduit and/or reservoir. This enables a new reservoir to be re-attached to the first valve. Alternatively, the first conduit may comprise a first portion and a second portion that are connected via a joint. The first portion of the first conduit may be permanently attached to the metering chamber. The second portion of the first conduit may be permanently attached to the prime chamber. The first portion of the first conduit may comprise the first valve.

In some embodiments, the reservoir may be refilled. For example, the reservoir may comprise a fourth valve. The fourth valve may be a refill valve. The refill valve may be located within the storage chamber. The refill valve may be configured to receive an external conduit. The external conduit may be a syringe or needle, for example. Consequently, fluid may be transferred from the external conduit and into the reservoir via the fourth valve. The fourth valve may be a one way valve.

The housing may comprise a hole configured to receive the external conduit. Consequently, the external conduit may pass through the housing before entering the fourth valve. Alternatively, the fourth valve may be mounted within the hole of the housing. This may improve the ease with which the reservoir can be refilled.

The housing may be manufactured from a metal, plastic, bioplastic, liquid wood and/or cardboard.

The present invention will now be described, by way of example only, with reference to the accompanying drawings in which.

Figure 1:
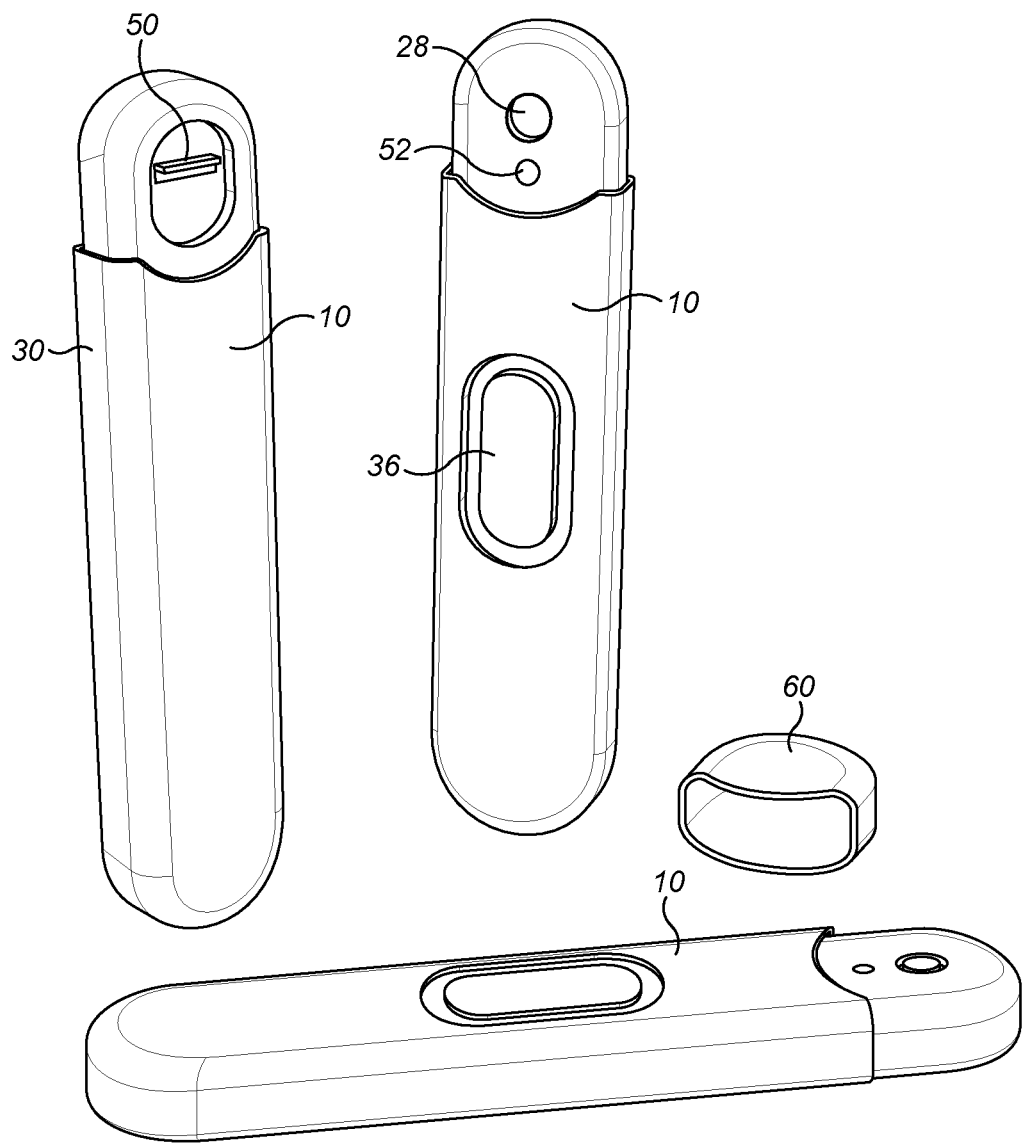
FIG. 1 shows three views of the device according to the present invention.

FIG. 1 shows three views of the exterior of a device 10 of the present invention. The device 10 is encapsulated by a housing 30. The housing 30 is elongate and is provided with a primer or primer button 36, an indicator 52 and a nozzle 28 on one side and a trigger 50 on the other side. The primer 36 is a lozenge or oval shaped piece that is actuated by pushing it inwards in order to prime the device 10 for the ejection of a dose of fluid, in particular a medicament such as a dose of eye medication, from the nozzle 28.

The indicator 52 provides visual confirmation to the user that the device is ready to dispense a dose of medicament. The indicator 52 in the illustrated example is a passive indicator. It is configured as a light guide that transmits light by total internal refraction if fluid is ready to be dispensed. In other embodiments, not illustrated in the accompanying drawings, the indicator may be a brightly coloured peg. Furthermore, in some embodiments not shown in the attached, the indicator may include one or more moving parts, such as, for example, the brightly coloured peg being configured to move to a more prominent position to show that the device is ready to dispense.

The trigger 50 is a bar shaped button that controls the release of the metered dose of medicament. The trigger 50 has a very short stroke of around 3 mm and can be deployed with the application of a low force. The force and stroke required are matched to other actuations familiar to the user so that there is a similar force required and a similar stroke to a keyboard key press. In some embodiments, this may be lowered to a level familiar from a smart phone home key, which typically requires around 1 N and a stroke of up to 1 mm.

The housing 30 is also provided with a reduced thickness section around the nozzle 28 to accommodate a cap 60 when the device 10 is not in use. The cap 60 has a width that substantially matches the housing 30 such that, when the cap 60 is on the device 10, the device 10 has a constant thickness, thus avoiding any stepped edges that could catch and cause the cap 60 to be accidentally removed.

Figure 2:
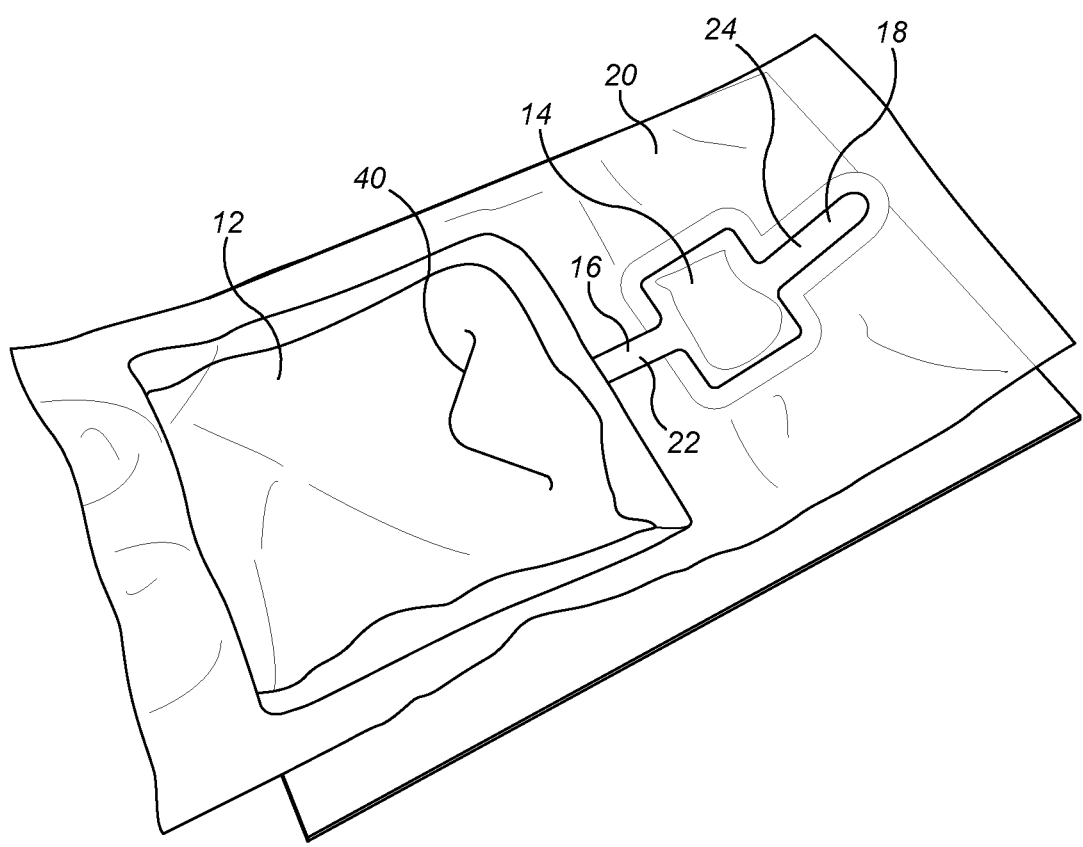
FIG. 2 shows a pouch deployed within the device similar to that shown of FIG. 1.

FIG. 2 shows a pouch 20 that is deployed within a housing 30 of the device 10 similar to that one illustrated shown in FIG. 1. The proportions are exemplary only and therefore a housing 30 of the device 10 configured to hold the illustrated pouch 20 of FIG. 2 would have different height to width ratio to accommodate the pouch. The pouch 20 is formed from two planar sheets of a flexible but substantially non-elastic polymer. For example, the pouch may be formed from metalised PET, or boppmet, which is a layered flexible polymer with a metalised film. When selecting the material, it is important that is it flexible, but does not stretch. This is important for the effective formation of the valves. Furthermore, the selected material must have a low gas permeability and low moisture vapour permeability. Most polymers allow oxygen/water vapour through and therefore the material must combine a plurality of layers, at least one of which must block transfer of moisture vapour and other gases. Some of the polymers utilised in the layered construction may have some level of elasticity, but the overall sheet should be substantially non-elastic.

Between the two polymer sheets there is provided a reservoir 12 that is sized to hold a plurality of doses of a medicament in liquid form and a metering chamber 14 that is sized to hold at least a single metered dose. When medicament flows into the metering chamber 14 it transforms between a rest state and a primed state. The difference in volume between these two states is a single metered dose. The overall volume of the metering chamber 14 is greater than a metered dose because the rest state does not practically equate to an empty metering chamber 14. For example, the volume of the metering chamber may be 120-150% of a metered dose because, in the rest state, 20-50% of a metered dose will remain in the metering chamber.

A first conduit 22 runs between the reservoir 12 and the metering chamber 14. The first conduit 22 includes a first valve 16, in this case a so-called winkle valve. A winkle valve is formed due to a difference in width between the reservoir 12 and the conduit 22. When the reservoir has liquid in it, this difference in width causes deformation of the polymer sheets resulting in creases in the conduit forming the winkle valve. These creases prevent fluid from flowing in either direction through the conduit 22 in which they are formed until a threshold pressure is exceeded causing the deformations to be overcome allowing some fluid to flow into the metering chamber 14.

A second conduit 24 runs between the metering chamber 14 and an outlet 26 (not shown in FIG. 2). The outlet 26 is a hole formed in one of the sheets of polymer material from which the pouch is fabricated, located in the second conduit and capable of permitting the ejection of fluid perpendicular to the plane of the pouch 20, i.e. approximately at right angles to the conduit 24.

The second conduit 24 includes a kink valve 18. The size and shape of the reservoir 12, metering chamber 14 and first and second conduits 22, 24 are defined by the extent to which the two substantially planar sheets from which they are formed are adhered together. In the illustrated example, the reservoir 12 and metering chamber 14 are both rectangular. However, in other examples, not shown in the accompanying drawings, the reservoir may take a different shape provided there is still the required step change in width between the reservoir and the conduit in order to create the first valve. For example, a funnel shaped reservoir that tapers strongly towards the conduit may fail to provide the step change in width required and may not be effective.

Conversely, a circular reservoir or a square with or without rounded edges would be effective.

In the illustrated example, the first valve 16 is a winkle valve. However, in some embodiments, it may be a combined winkle and kink valve, in that, as the metering chamber fills at least part of the metering chamber moves perpendicular to the plane of the pouch, which is substantially parallel to the plane of the housing 30 when the pouch 20 is in the rest state, i.e. in an upward direction when the pouch 20 is configured as shown in FIG. 2. In some embodiments, not illustrated in the accompanying drawings, the valve may be solely a kink valve. This is applicable if the device 10 is very elongate so that the width of the reservoir 12 is comparatively small relative to its length and therefore the step change in width between the width of the reservoir and the width of the conduit is insufficient for a winkle valve to form.

The pouch 20 also includes a burstable seal 40 (shown burst) that remains intact until the first use of the device 10. The burstable seal 40 protects the first valve 16 from fatigue or excess pressure experienced when the device is being manufactured, transported and stored prior to first use. The burstable seal 40 also protects the contents of the reservoir 12 by retaining them in the part of the reservoir 12 furthest from the conduit 22.

Figure 3:
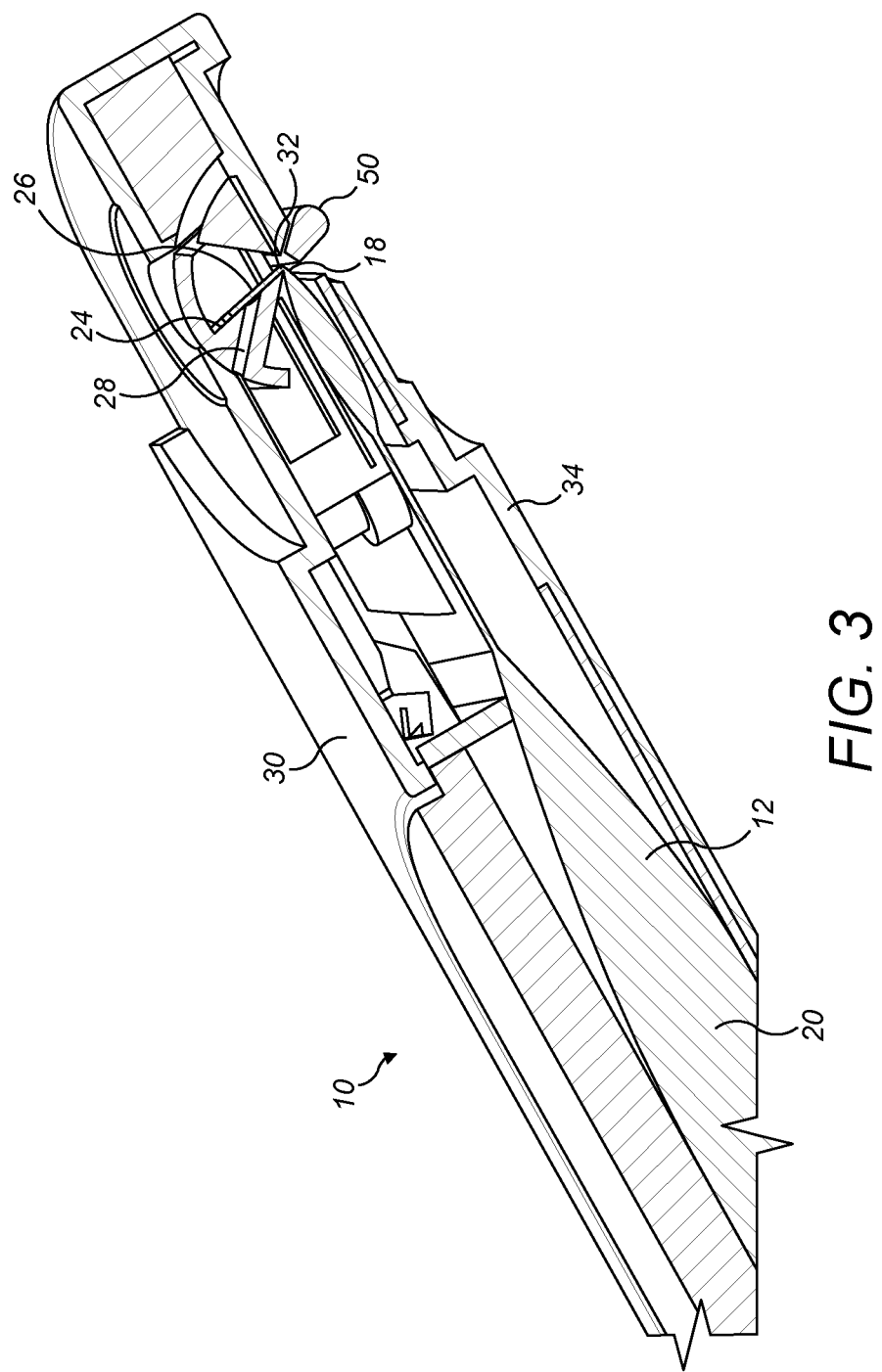
FIG. 3 shows a cut through cross section of part of the device of FIG. 1.

FIG. 3 shows a cut through section of the device 10 showing both the housing 30 and contents. The reservoir 12 is shown filled with fluid so that the two planar sheets from which the pouch 20 is formed deform so that the pouch 20 abuts the primer 36 provided in the housing 30 prior to first usage. The metering chamber 14 is also shown in a filled condition so that it has deformed the formerly flat sheets to form a lozenge shape. Subsequent to first usage and prior to second and subsequent usages, the pouch 20 may not actually abut the primer 36, but provided the primer 36 can still act on the pouch 20 it remains fit for function.

The housing 30 is provided with a planar wall 34 onto which at least part of the pouch 20 is affixed. The trigger 50 slots over the pouch 20 and into the housing 30 and at least partially protrudes therefrom to enable the user to actuate the kink valve 18 and thereby dispense the dose through the nozzle 28 which is also formed within the trigger 50. The trigger 50 is provided with a slot through which the conduit 24 is threaded. The slot provides an edge 32 over which the second conduit is folded in order to manage the opening and closing of the kink valve 18. The provision of the edge 32 defines the position of the kink valve 18 and also modifies the angle at which the valve is opened and closed. The user's urging of the trigger 50 unfolds the second conduit 24 from the edge 32 and thereby directly actuates the kink valve 18 to release the metered dose of fluid from the metering chamber 14. The fluid flows along the second conduit 24 through the kink valve 18 and then out of the device 10 through the nozzle 28 provided at the outlet 26.

Figure 4:
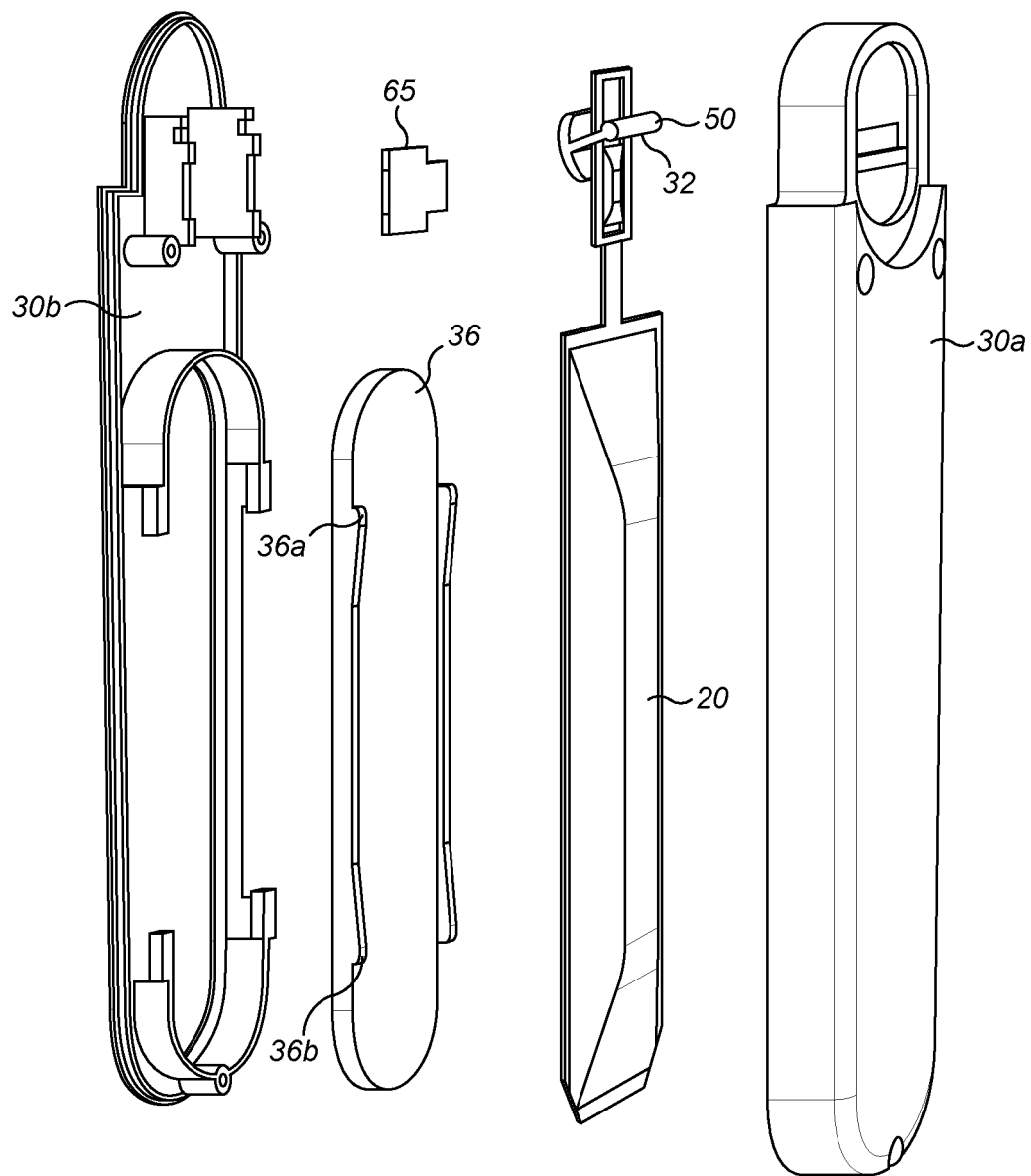
FIG. 4 shows an exploded view of the components forming the device of FIG. 1.

FIG. 4 is an exploded view of the parts that make up the device 10. The housing 30 is formed from two pieces 30a and 30b. The first piece, or lower piece, 30a includes an opening through which the trigger 50 protrudes when the device 10 is assembled. The second piece or top piece 30b includes a cut out to accommodate the primer 36 and an opening that forms the nozzle 28.

The primer 36 is a separate piece that is sandwiched between the first and second pieces 30a, 30b of the housing 30. The primer 36 includes a primer button. The primer 36 may be sprung. More specifically, the primer 36 is provided with a plurality of leaf springs configured to spring the button away from the reservoir 36a and 36b. From this separated position, the user can push the primer 36 inward towards the centre of the housing in order to overcome the spring force. This pressurises the reservoir 12, thereby allowing fluid to move into the metering chamber so that the metering chamber is filled with at least a single metered dose.

The trigger 50 is provided on a separate piece, which is bonded to the pouch 20 in the vicinity of the second conduit and kink valve 18. The trigger 50 pivots relative to the housing 30 so that the second conduit 24 is urged over the edge 32 thus opening or closing the kink valve. In other examples, not illustrated in the accompanying drawings, the trigger may not be bonded to the pouch.

The metering chamber spring 65 is a metal leaf spring. The metal leaf spring 65 is provided to bias the metering chamber 14 to a flat configuration in which it is not filled. It may still comprise some fluid in this configuration, but this is the reduced fluid configuration to which the device is biased. It is this spring 65 that forces the dose of medicament out of the device 10 when the kink valve 18 is opened.

Figure 5A:
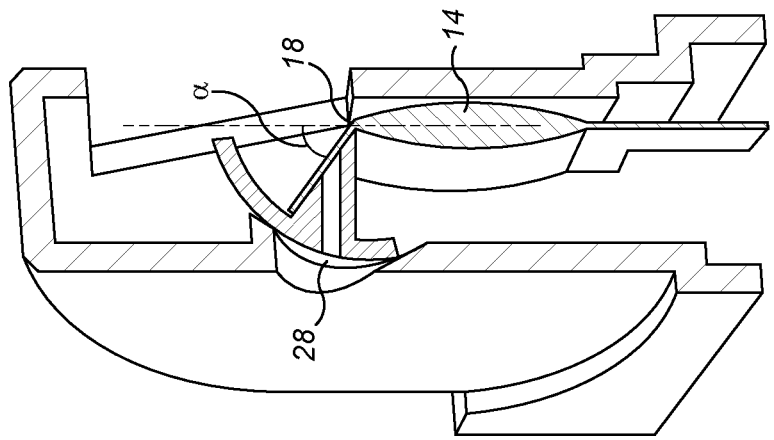
FIGS. 5A and 5B show the kink valve in the closed and dispensing positions respectively.
Figure 5B:
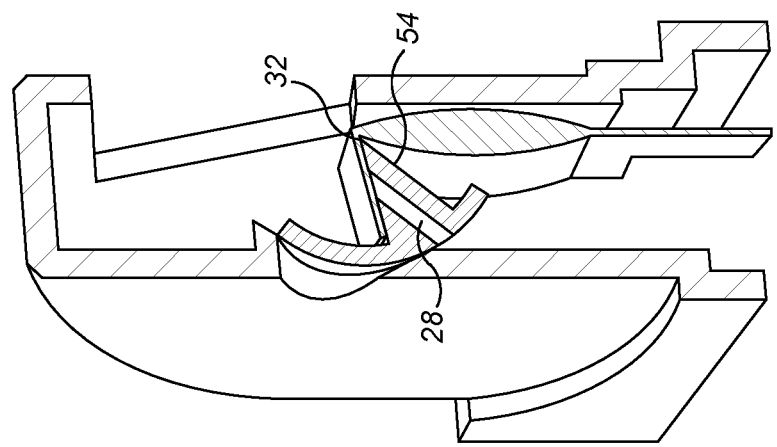

FIGS. 5A and 5B show the detail of the kink valve 18 in a closed and open configuration, respectively. When the kink valve 18 is closed (FIG. 5A), the second conduit 24 is folded over the edge 32 forcing the conduit to kink, preventing fluid flow. The metering chamber 14 is full showing that a dose of fluid medicament is ready to be dispensed. The edge 32 is provided on a rocker 54 that pivots between an open position and a closed position.

When the device is triggered, the rocker 54 rotates about its pivot point and changes the angle of the second conduit so that it passes the opening angle of the kink valve 18. The opening angle α of the valve is defined as being the angle of the part of the second conduit that lies beyond the edge 32 relative to the housing 30. The angle α is shown in FIG. 5B. It this example it is around 140° when the valve is closed and the angle is reduced to open the valve. The difference in angle between open and closed is in the region of 20° and 70°. One of the advantages of the use of a kink valve in this context, is that the valve does not have to be turned through a specific, predefined angle to actuate. Instead, it simply has to be turned past the opening threshold value for the valve. It does not matter if the conduit is further rotated, the valve will remain open. All that is critical is that it passes the opening angle. This makes the functionality of the valve much more capable of withstanding manufacturing tolerances and other inaccuracies whilst still working correctly. In addition, this functionality results in a low actuation force and also minimises the part count.

The rocker 54 is provided with a nozzle 28 through which the fluid is dispensed from the device 10. The nozzle 28 has a constant cross section and it links the outlet 26 of the second conduit 24 to the exterior of the housing 30. In other embodiments, not illustrated in the accompanying drawings, the nozzle may be tapered to increase the velocity of the fluid as it exits the device 10. The shape and configuration of the nozzle 28 influences the speed at which the fluid is dispensed from the device 10. In addition, the shape and configuration of the nozzle can influence a form factor of the fluid as it leaves the device 10. In particular, the fluid may leave the device 10 as a single drop or as a plurality of small droplets or as a fine spray.

The shape and configuration of the nozzle can also control the intended direction of the spray of fluid that exits the device 10. As indicated in both FIGS. 5B and 6B, the fluid is intended to be dispensed horizontally. However, depending on the configuration of the nozzle the fluid can be dispensed with an upward trajectory. It is important, to achieve control over the trajectory of the dispensed fluid, that the fluid is dispensed at a speed and in a direction in which the surface tension of the fluid does not affect the dispensing. In summary, the fluid must be positively dispensed or ejected from the device 10, it must not collect on an outer surface of the housing from which it can then drip.

Figure 6A:
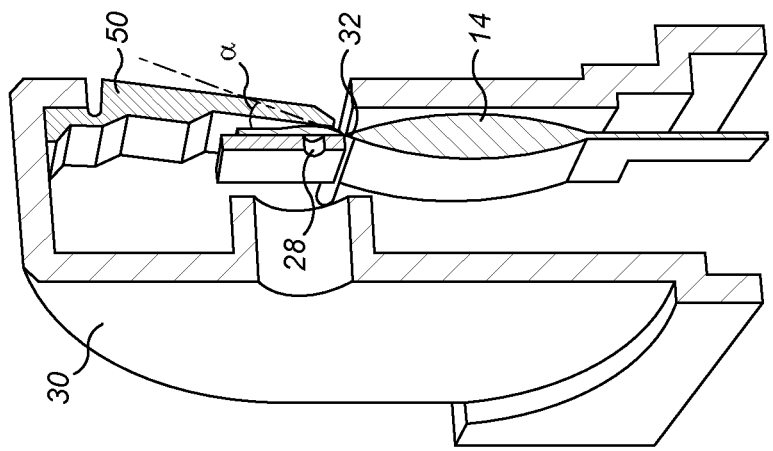
FIGS. 6A and 6B show an alternative configuration of the kink valve and dispensing nozzle.
Figure 6B:
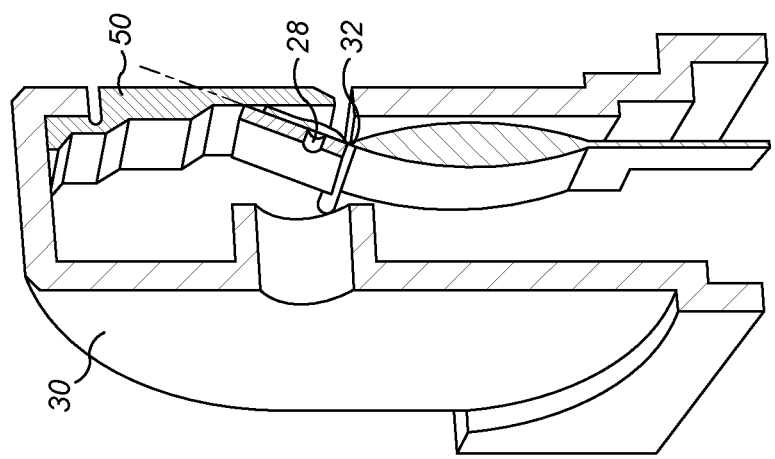

FIGS. 6A and 6B show an alternative configuration for the kink valve 18. In this configuration, the trigger 50 is attached to the end of the housing 30 and pivots by a comparatively small angle in order to actuate the kink valve 18. In this configuration, sometimes referred to as a "reverse kink", the conduit 24 is still folded over the edge 32, but in the reverse direction from the embodiment shown in FIG. 5. The user presses the trigger 50 inwards in the same direction as they expect the fluid to be dispensed. This is therefore a very natural action for the user. The horizontal distance of travel of the end part of the trigger 50 is about 2 mm. This is within the intuitive range of the user to push such buttons or triggers. The angular difference between the open and closed position is only around 20° to 70°. The nozzle 28 is provided in the form of a through hole that guides the fluid from the conduit 24 and out of the device 10 in line with the other configuration described above in conjunction with FIGS. 5A and 5B. In other similar versions of this configuration, not illustrated, the horizontal travel may be 0.5 mm, 0.6 mm, 1 mm, 1.5 mm, 2 mm or 3 mm. These distances are similar to other user actuated buttons such as keyboard presses and smart phone home key presses. The user will therefore find this extent of movement intuitive. The opening angle may be 15°, 20°, 25° or 30°.

Figure 7:
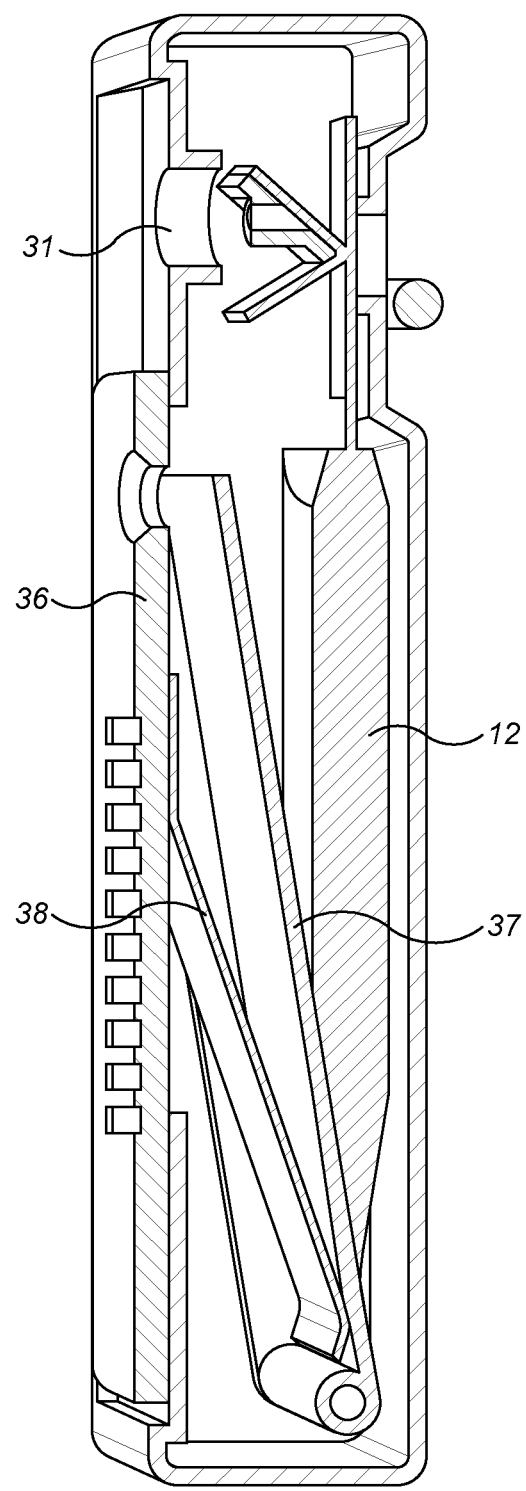
FIG. 7 shows cut through cross section of the device showing an alternative example of the primer.

FIG. 7 shows an alternative primer 36. The primer 36 is actuated by the user sliding the primer 36 towards the nozzle 28. The primer 36 has, attached to its underside, within the housing 30 a hook-shaped portion 38 that impinges on a spreader 37 that is provided to distribute the force from the hook-shaped portion 38 equally across the width of the reservoir. The spreader 37 is pivotably connected to the housing 30 in the vicinity of the reservoir 12. The combination of the hook-shaped portion 38 and the spreader 37 is arranged to ensure that no pressure is applied to the reservoir when the primer 36 is slid back to its neutral or starting position. This ensures that fluid is only urged through the first valve 16 into the metering chamber 14 on the priming stroke, i.e. the movement of the primer 36 towards the nozzle 28.

Figure 8B:
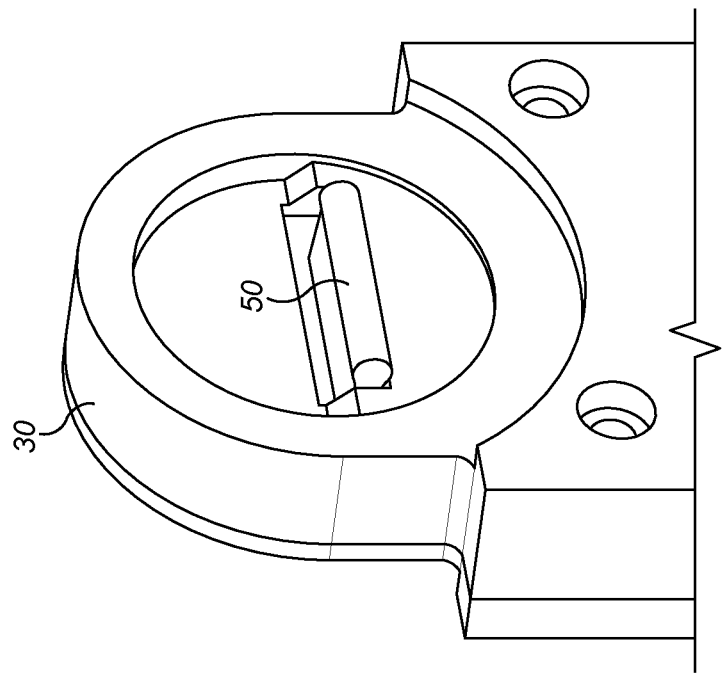
FIGS. 8A and 8B show the trigger before and after actuation, respectively.
Figure 8A:
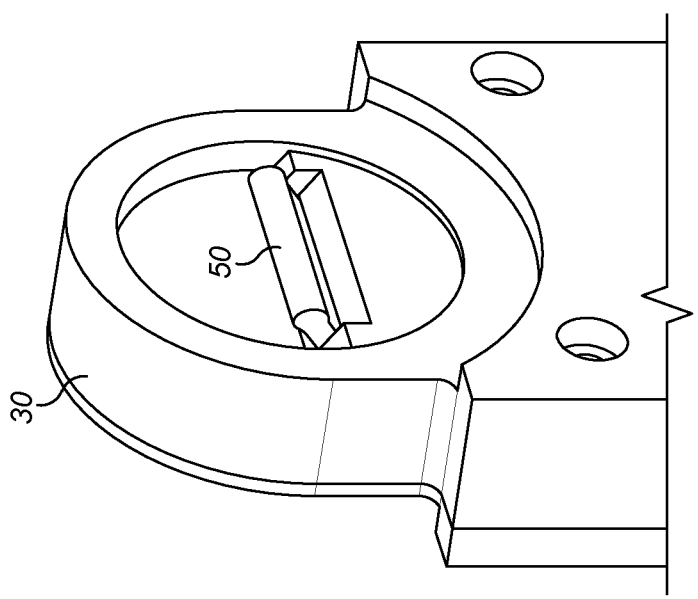

FIG. 7 also shows a cowl 31 that is provided in the housing 30 around the nozzle 28 to shield the nozzle. FIGS. 8A and 8B show the trigger 50 ready to be deployed, and subsequent to deployment, respectively.

The stroke is very short, only around 3 mm which is less than the typical stroke of a computer keyboard. It can therefore be actuated by an intuitive amount of movement from the user.

Figure 9:
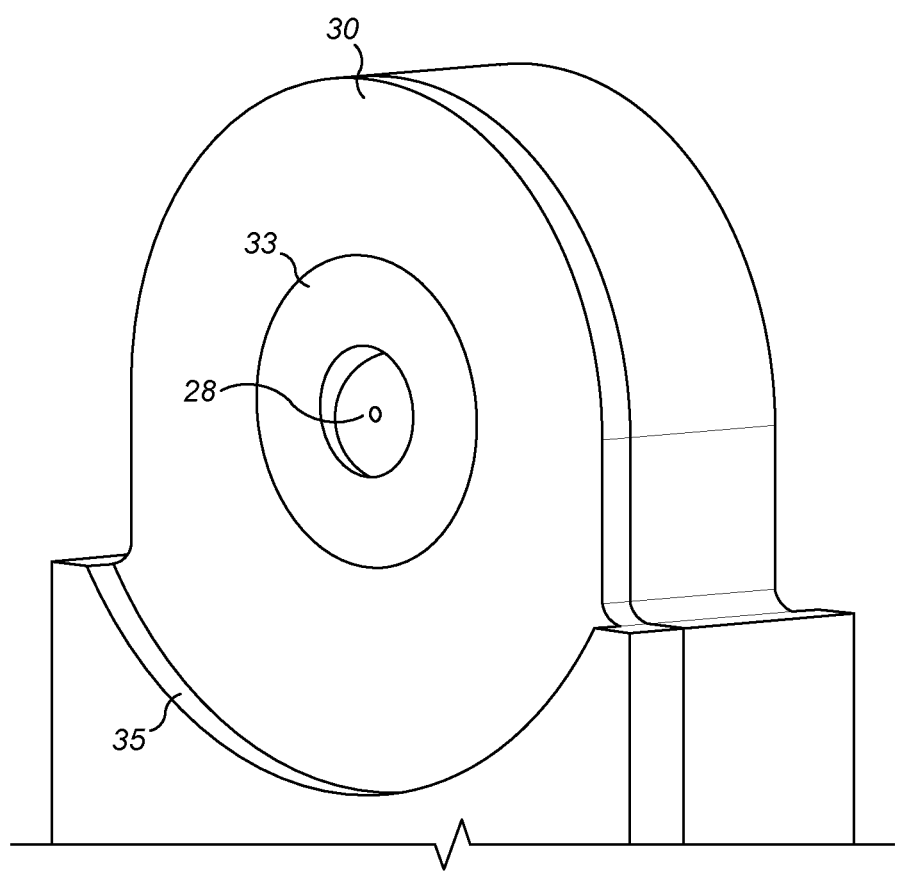
FIG. 9 shows the aiming aid and outlet.

FIG. 9 shows the side of the housing comprising the nozzle 28 and also including an aiming aid 33. The aiming aid 33 consists of a bright ring of colour that encircles the nozzle 28. Although, in use, the aiming aid 33 is too close to the eye for the user to focus on it, nevertheless it gives the user positive confirmation that the device 10 is correctly aligned to dispense the metered dose into the eye. If the device is correctly aligned, the user will see a bright ring of colour which allows the user to aim the device so that the medicament will be dispensed into the eye. In some variants the aiming aid may be offset from the nozzle such that when the aiming aid is aligned with the user's eye the liquid medicament is dispensed to a point offset from the centre of the eye in an area that may be less sensitive for the user.

Furthermore, FIG. 9 shows a lip 35 that engages with the cap 60 when the device 10 is not in use.

Figure 10:
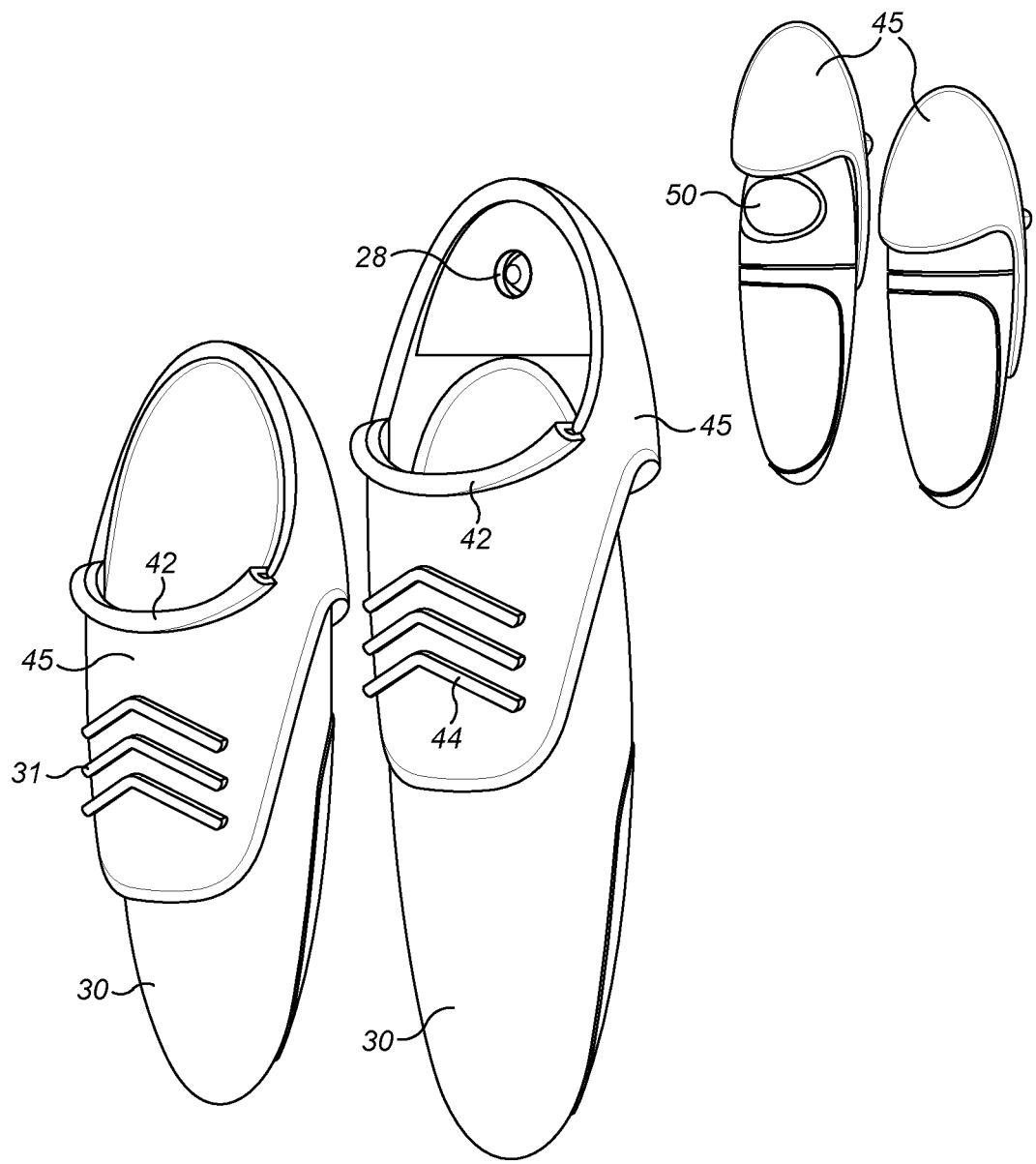
FIG. 10 shows front and back views of the device 10 in both the storage condition and the primed or activated condition.

FIG. 10 shows an alternative example of the device 10. FIG. 10 shows front and back views of the device 10 in both the storage condition and the primed or activated condition. In this example, the housing 30 is augmented by a sleeve 45 including a surface 42 provided to interface with and pull down the user's lower lid in order to make a conjunctival sack to hold the dose once dispensed to prevent it from flowing away from the user's eye. The sleeve 45 also includes ridges 44 that are designed to interface with the user's thumb, the arrow shape confirming to the user that this is the correct direction in which to push the ridges 44 to move the sleeve 45 relative to the housing 30 to reveal the nozzle 28 through which the metered dose of medicament will be dispensed. The provision of ridges 44 also ensures that the user's thumb doesn't slip off the sleeve 45.

Figure 11A:
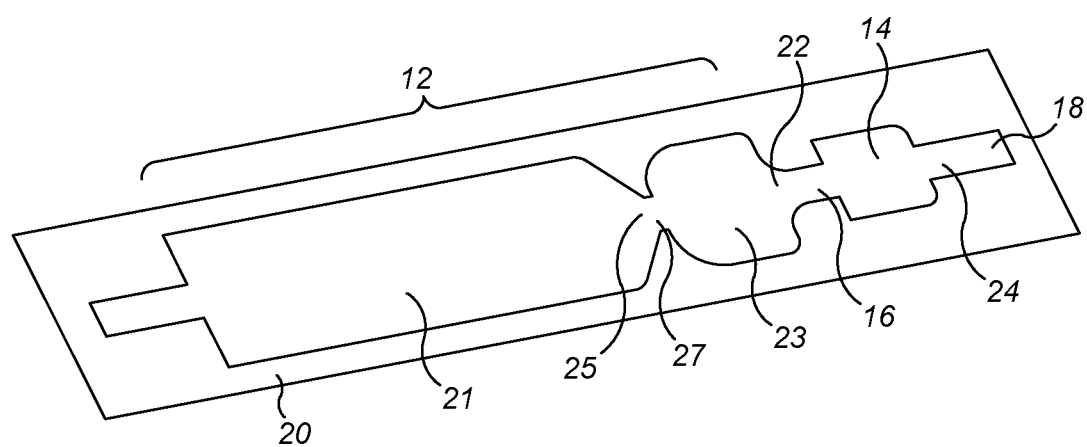
FIG. 11A shows a pouch comprising a storage chamber and a prime chamber.

FIG. 11A shows a pouch 20 comprising a storage chamber 21 and a prime chamber 23. More specifically, the reservoir 12 comprises a storage chamber 21 and a prime chamber 23. Each of the storage chamber 21 and prime chamber 23 are sized to hold a plurality of doses of a medicament in liquid form.

Figure 11B:
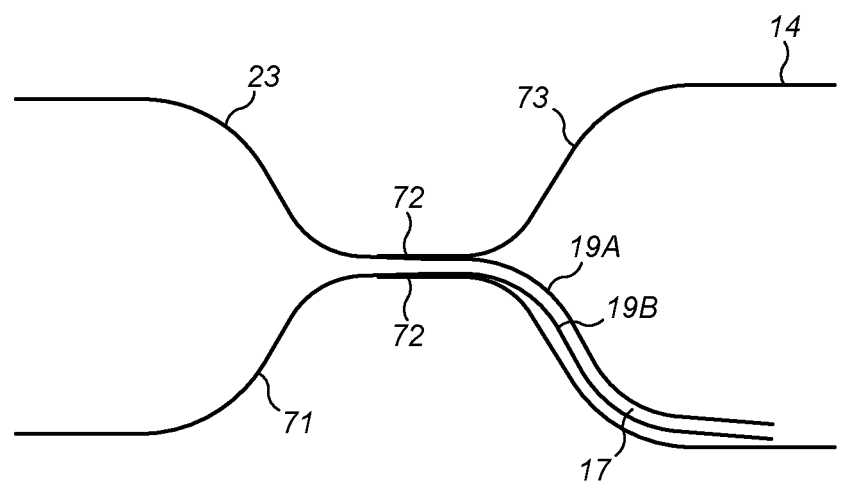
FIG. 11B shows a section through a pouch comprising a flat valve between the prime chamber and the metering chamber.

The first conduit 22 runs between the prime chamber 23 and the metering chamber 14. The first conduit 22 includes the first valve 16. The first valve 16 is a flat valve 17, as shown in FIG. 11B. The second conduit 24 runs between the metering chamber 14 and an outlet 26 (not shown in FIG. 11A). The second conduit 24 includes the second valve 18. The second valve 18 is a kink valve, as previously disclosed.

The pouch 20 further comprises a third conduit 25 that runs between the storage chamber 21 and the prime chamber 23. The third conduit 25 comprises a third valve 27. The third valve 27 is a kinked pinch valve. The kinked pinch valve 27 comprises two tessellating surfaces configured to manipulate the third conduit 25 into a kinked shape between the two surfaces when the valve 27 is actuated.

Each of the two surface of the valve comprises an angle that is greater than the actuation angle of the third conduit 25. Consequently, when the third valve is closed, the third conduit is pinched between the two surface and forms a kinked shape around the angle of the surface.

FIG. 11B shows a section through the pouch 20 comprising a flat valve 17 between the prime chamber 23 and the metering chamber 14. The flat valve 17 comprises two pieces of material 19A, 19B laid flat against each other. The two pieces of material 19A, 19B protrude into the metering chamber 14 and are configured to form a one-way valve therein. Consequently, as the pressure in the metering chamber 14 increases, the pressure on the outside of the each of the two pieces of material 19A, 19B pushes two pieces of material against each other and forms a seal. This prevents the fluid flowing from the metering chamber 14 back into the prime chamber 23. The two pieces of material 19A, 19B are a part of the pouch 20. More specifically, the two pieces of material 19A, 19B are a part of a distinct reservoir pouch 71. Consequently, the join 72 between the external surface of the reservoir pouch 71 and the internal surface of the metering pouch 73 is welded, adhered or bonded together, thus preventing the flow of fluid therebetween.

Figure 12:
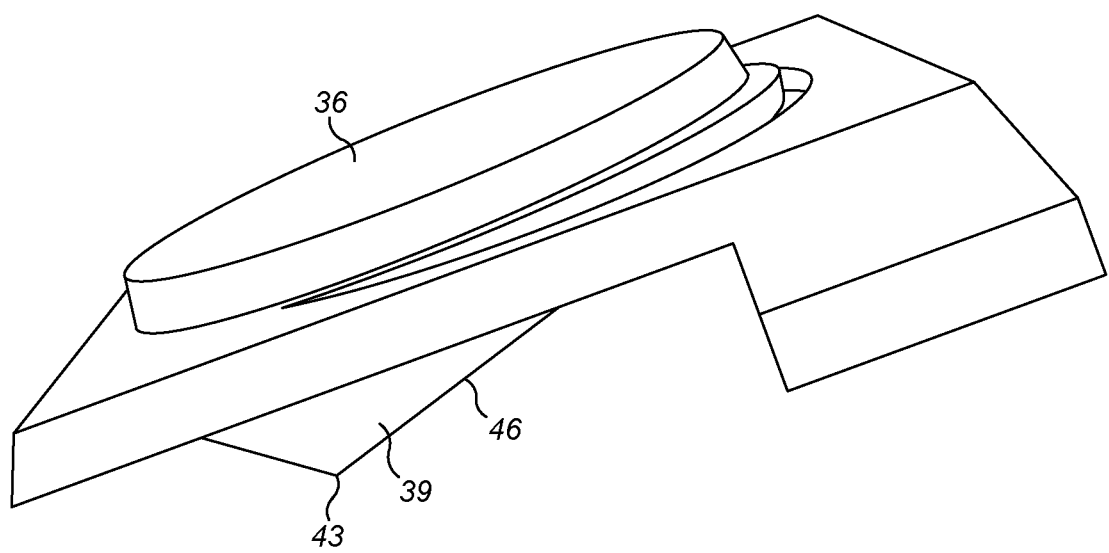
FIG. 12 shows a primer according to some embodiments of the invention.

FIG. 12 shows a primer button 36 according to some embodiments of the invention. The primer, or primer button, 36 is a lozenge or oval shaped piece that is actuated by pushing it inwards in order to prime the device 10 for the ejection of a dose of fluid, in particular a medicament such as a dose of eye medication, from the nozzle 28.

The primer 36 is first pushed downwards, or inwards, to actuate the third valve 27, thus sealing the prime chamber 23. Subsequently, the primer 36 is configured to rotate in order to urge fluid from the prime chamber 23 into the metering chamber 14. The primer 36 comprises a protrusion 39 configured to actuate the third valve 27. Once the third valve 27 has been actuated, the primer 36 is configured to rotate about the tip 43 the protrusion 39, thus urging fluid from the primer chamber 23 into the metering chamber 14.

Moreover, the protrusion 39 comprises a sprung surface 46 configured to contact the prime chamber during the actuation of the primer. The sprung surface may comprise a spring. Alternatively, or in addition, the sprung surface may be formed from a soft material, such as foam. Consequently, the sprung surface 46 is configured to limit the pressure applied to the prime chamber 23.

Figure 13A:
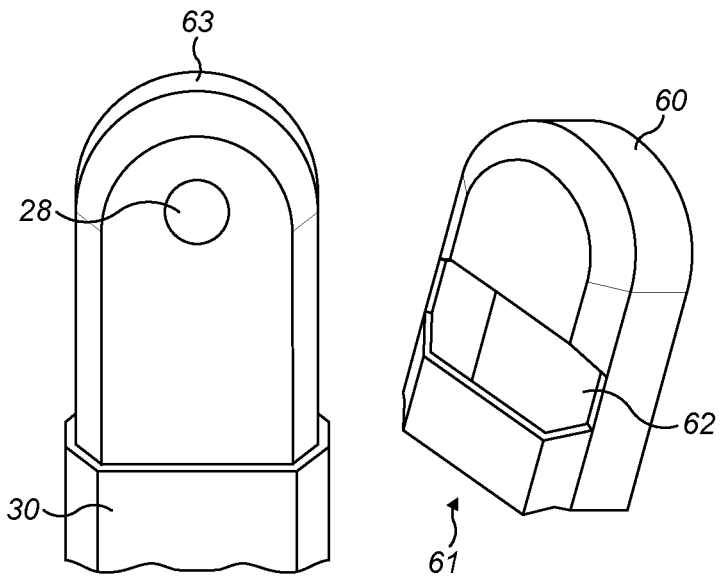
FIG. 13A shows a device according to some embodiments of the invention.
Figure 13B:
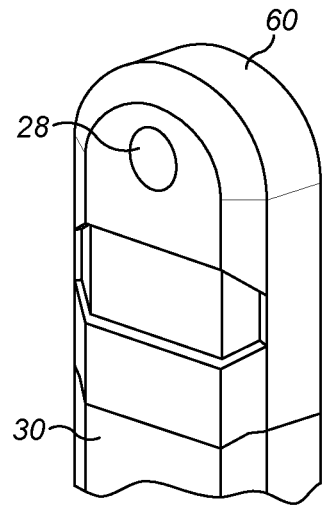
FIG. 13B shows the device of FIG. 13A further comprising a cap in a first orientation.
Figure 13C:
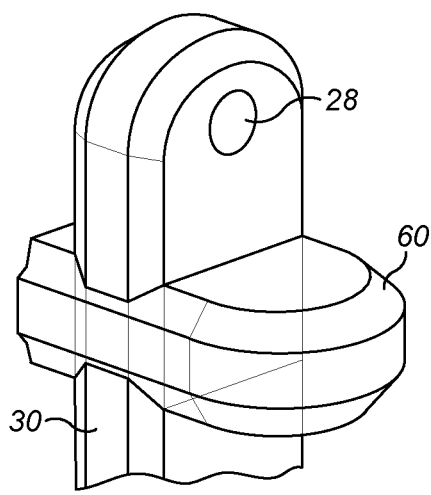
FIG. 13C shows the device of FIGS. 13A and 13B comprising a cap in a second orientation.

FIGS. 13A-C shows a device 10 according to some embodiments of the invention. The device 10 is encapsulated by an elongate housing 30 having a nozzle 28 on one side and a trigger 50 (not shown in FIGS. 13A-C) on the other side.

The device further comprises a cap 60. The cap 60 is configured to engage with the housing 30 in a first orientation, as shown in FIG. 13B, and a second orientation, as shown in FIG. 13C. Accordingly, the cap 60 comprises a first aperture 61 configured to receive and enclose the end of the device 63. Consequently, the cap 60 covers the nozzle 28 when in the first orientation, as shown in FIG. 2B. Moreover, the housing 30 is provided with a reduced thickness section around the nozzle 28 to accommodate the cap 60 within the first orientation, as shown in FIG. 13B. The cap 60 has a width that substantially matches the housing 30 such that, when the cap 60 is on the device 10 in the first orientation, the device 10 has a constant thickness, thus avoiding any stepped edges that could catch and cause the cap 60 to be accidentally removed.

Moreover, the cap 60 comprises a second aperture 62. The second aperture 62 is a hole that extends through the entire width of the cap. Consequently, the cap 60 is configured to slide over the end of the device 63 in a second orientation, thus leaving the end of the device 63 and nozzle 28 exposed, as shown in FIG. 13C.

Figure 14C:
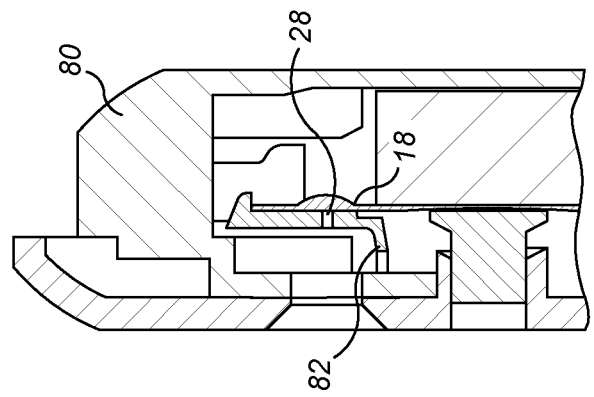
FIG. 14C shows the trigger of FIGS. 14A and 14B once the actuation has been completed.
Figure 14B:
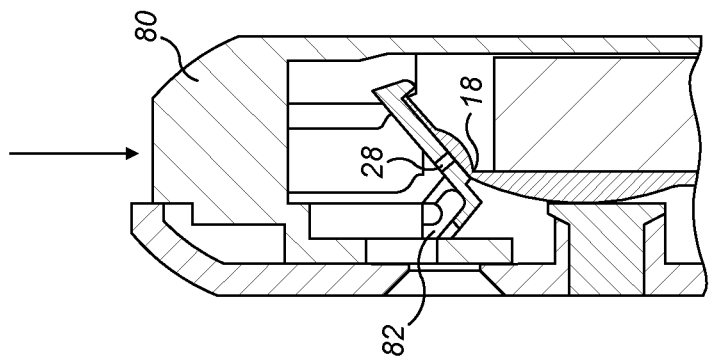
FIG. 14B shows the trigger of FIG. 14A mid-actuation.
Figure 14A:
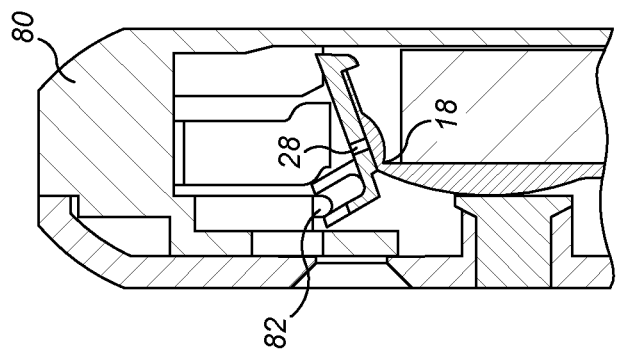
FIG. 14A shows an alternative configuration of the trigger.

FIGS. 14A-C show some embodiments wherein the trigger 50 is in the form of a dispenser button 80. The button 80 is shaped and positioned such that it covers the outlet port when the fluid is not being dispensed. This protects the outlet port when the device is not in use. In the embodiment illustrated in FIGS. 14A-C, the outlet port is fully occluded when the fluid is not being dispensed. In other embodiments, not shown in the accompanying drawings, the occlusion may be partial.

The dispenser button 80 comprises a dispenser button spring configured to bias the dispenser button in its undepressed position, as shown in FIG. 14A. The dispenser button spring is an over centre spring. Consequently, the force ramp down on the spring is so quick that the user is forced to press the dispenser button or trigger 50 at a fast rate. The over centre spring is configured to flip from an 'n' shape to a 'u' shape via a second order wave shape as the dispenser button is depressed into the position shown in FIG. 14C. The second order wave shape is a rotated 's' or '~' shape. As the over centre spring swaps from the second order wave shape to the 'u' shape the dispenser button or trigger 50 is forced through at a rapid rate to make sure the kink valve 18 is fully open for the duration of the dispense, as shown in FIG. 14C. It is important that the kink valve unfolds fully, to a pre-set position, as shown in FIG. 14C, before any fluid is released because the direction of the fluid would be altered if the nozzle 28 was still moving when the fluid started to be ejected. Moreover, the over centre spring is configured to return the trigger 50 to its original position following actuation.

The dispenser button 80 comprises a cam 82. Consequently, the line of actuation of the dispenser button 80 may move closer to the nozzle's pivot as the trigger is pressed. This increases the angular rotation of the nozzle 28 for a given trigger displacement.

Figure 15:
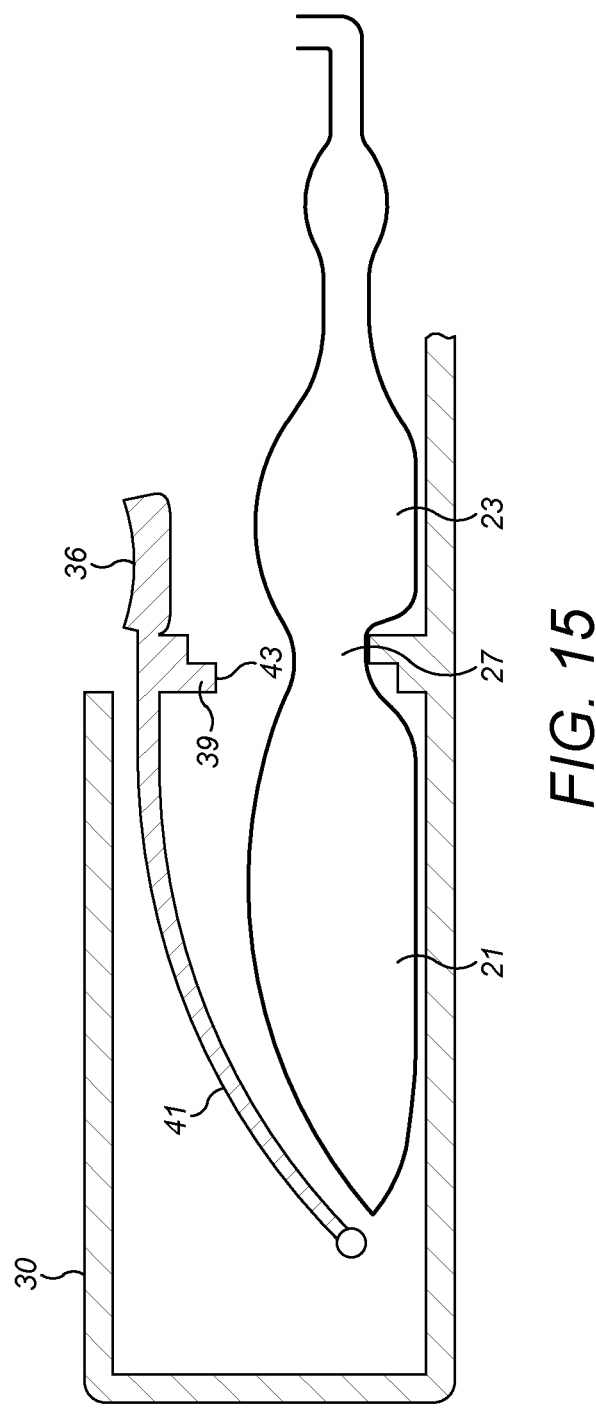
FIG. 15 shows an alternative configuration of the primer.

FIG. 15 shows an embodiment of the present invention comprising a primer button 36 further having an arm 41. The primer, or primer button, 36 is actuated by pushing it inwards in order to prime the device 10, as previously described. Initially, as the primer 36 is actuated, the primer button 36 and arm 41 move downwards, thus applying a pressure to the storage chamber 21 of the reservoir 12. As the primer 36 is actuated further, the tip 43 of the protrusion 39 is configured to actuate the third valve 27, thus sealing the prime chamber 23 from the storage chamber 21. Subsequently, as the primer 36 is further actuated, the primer 36 is configured to rotate about the tip 43 the protrusion 39, thus urging fluid from the primer chamber 23 into the metering chamber 14. Consequently, the storage chamber remains non-pressurised until the primer 36 is actuated.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

It will further be appreciated by those skilled in the art that although the invention has been described by way of example with reference to several embodiments. It is not limited to the disclosed embodiments and that alternative embodiments could be constructed without departing from the scope of the invention as defined in the appended claims.

The invention claimed is:

1. A device for dispensing a metered dose of fluid, the device comprising a housing comprising:
   a non-pressurised reservoir sized to accommodate a plurality of doses of fluid;
   a spring-loaded metering chamber sized to hold at least a single dose of fluid;
   a first valve enabling fluid communication between the non-pressurised reservoir and the spring-loaded metering chamber;
   a kink valve enabling the fluid in the spring-loaded metering chamber to exit the device; and
   a flexible pouch in which the non-pressurised reservoir is formed,
   wherein the flexible pouch also includes the spring-loaded metering chamber and the kink valve.

2. The device according to claim 1, wherein the first valve is a non-return valve.

3. The device according to claim 1, wherein the non-pressurized reservoir comprises a storage chamber and a prime chamber separated by a third valve.

4. The device according to claim 1, wherein the pouch is formed from a plurality of layers of different polymers.

5. The device according to claim 1, wherein the housing includes a substantially planar wall to which at least part of the pouch is affixed.

6. The device according to claim 1, wherein the first valve is formed in a first conduit linking the non-pressurised reservoir and the spring-loaded metering chamber and wherein the kink valve is formed in a second conduit linking the spring-loaded metering chamber and an outlet.

7. The device according to claim 6, wherein the outlet is provided with a nozzle.

8. The device according to claim 6, wherein the first and/or second conduit has a constant width.

9. The device according to claim 7, wherein the nozzle is configured to ensure that the metered dose of fluid is ejected from the device.

10. The device according to claim 7, wherein the housing is provided with a cowl to protect the nozzle.

11. The device according to claim 1, wherein the housing includes a trigger configured to actuate the kink valve and thereby dispense the metered dose of fluid from the device.

12. The device according to claim 11, wherein the trigger is configured to block the outlet when the device is not dispensing the metered dose.

13. The device according to claim 1, wherein the kink valve has an actuation angle of between 20° and 70°.

14. The device according to claim 1, wherein the non-pressurised reservoir further comprises a burstable seal.

15. The device according to claim 1, wherein the housing further includes a primer configured to cause the fluid to pass through the first valve in order to enable fluid flow from the non-pressurised reservoir into the spring-loaded metering chamber.

16. The device according to claim 15, wherein the primer includes a sliding part which applies pressure to the non-pressurised reservoir as the sliding part moves in a first direction.

17. The device according to claim 1, wherein the housing further comprises an aiming aid.

18. The device according to claim 1, wherein the housing is provided with a surface that is designed to pull the user's lower lid down and hold it down.

\* \* \* \* \*